United States Patent
Koifman et al.

(10) Patent No.: US 10,561,464 B2
(45) Date of Patent: Feb. 18, 2020

(54) LASER TREATMENT SYSTEM AND COOLING DEVICE

(71) Applicant: LUMENIS LTD., Yokneam Ilit (IL)

(72) Inventors: Danny Koifman, Simtat Yuvalim (IL); Shaul Levy, Ahuzat Barak (IL); Igal Igor Koifman, Yokneam Ilit (IL); Uri Voitsechov, Yokneam Ilit (IL)

(73) Assignee: LUMENIS LTD. (IL)

(*) Notice: Subject to any disclaimer, the term of this patent is extended or adjusted under 35 U.S.C. 154(b) by 418 days.

(21) Appl. No.: 15/484,861

(22) Filed: Apr. 11, 2017

(65) Prior Publication Data

US 2017/0273744 A1     Sep. 28, 2017

Related U.S. Application Data

(63) Continuation-in-part of application No. 15/089,672, filed on Apr. 4, 2016, which is a continuation of (Continued)

(30) Foreign Application Priority Data

Oct. 8, 2013  (GB) .................................. 1317752.2

(51) Int. Cl.
  *A61B 18/20*  (2006.01)
  *A61N 5/06*  (2006.01)
  (Continued)

(52) U.S. Cl.
  CPC .......... *A61B 18/203* (2013.01); *A61N 5/0616* (2013.01); *A61B 2018/00023* (2013.01); (Continued)

(58) Field of Classification Search
  CPC .......... A61B 18/203; A61B 2017/0046; A61B 2017/00464; A61B 2017/00473; (Continued)

(56) References Cited

U.S. PATENT DOCUMENTS

| | | |
|---|---|---|
| 5,728,090 A | 3/1998 | Martin |
| 2007/0198004 A1 | 8/2007 | Altshuler et al. |

(Continued)

FOREIGN PATENT DOCUMENTS

| | | |
|---|---|---|
| KR | 20120073070 | 7/2012 |
| WO | 2007007167 | 1/2007 |

(Continued)

*Primary Examiner* — Eugene T Wu
(74) *Attorney, Agent, or Firm* — ISUS Intellectual Property PLLC (57) ABSTRACT

A laser treatment apparatus includes a primary handset and an auxiliary handset; the primary handset is connectable to the auxiliary handset; the primary handset has a laser source with a primary heat exchanger, and a main cooling circuit to provide cooling fluid to the primary heat exchanger to cool the laser source; the cooling circuit has a circuit connection for engagement with the auxiliary handset. The circuit connection comprises one or more fluid connectors for connection to an auxiliary cooling circuit within the auxiliary handset and the cooling circuit within the auxiliary handset includes a secondary heat exchanger. An electromechanical mechanism within the primary handset switches from a first position so that cooling fluid flows in the main cooling circuit within the primary handset when no auxiliary handset is attached and in a second position diverts flow of the cooling fluid to the heat exchanger in the auxiliary handset when the auxiliary handset is connected to the primary handset.

7 Claims, 11 Drawing Sheets

Related U.S. Application Data application No. PCT/IB2014/065112, filed on Oct. 7, 2014.

(60) Provisional application No. 62/325,008, filed on Apr. 20, 2016.

(51) Int. Cl.
 *A61B 18/00* (2006.01)
 *A61N 5/00* (2006.01)
 *A61N 5/067* (2006.01)

(52) U.S. Cl.
 CPC ............... *A61B 2018/00291* (2013.01); *A61B 2018/00452* (2013.01); *A61B 2018/202* (2013.01); *A61N 2005/005* (2013.01); *A61N 2005/067* (2013.01); *A61N 2005/0644* (2013.01)

(58) Field of Classification Search
 CPC ........... A61B 2018/00005; A61B 2018/00023; A61B 2018/00452; A61B 2018/00464; A61B 2018/0047; A61B 2018/00476; A61B 2018/0231; A61B 2018/202; A61B 2018/2253; A61B 2018/2255; A61B 2018/2285; A61N 5/0616; A61N 2005/002; A61N 2005/005; A61N 2005/0644; A61N 2005/067

See application file for complete search history.

(56) References Cited

U.S. PATENT DOCUMENTS

2013/0197495 A1* 8/2013 Koifman .................. A61N 5/06
 606/17
2013/0289558 A1* 10/2013 Reid, Jr. ............ A61B 18/1477
 606/41

FOREIGN PATENT DOCUMENTS

WO 2008012519 1/2008
WO WO-2015052645 A1 * 4/2015

* cited by examiner

LASER TREATMENT SYSTEM AND COOLING DEVICE

RELATED APPLICATIONS

This application is related to and claims priority to U.S. Provisional Application Ser. No. 62/325,008, filed Apr. 20, 2016, the entire disclosure of which is herein incorporated by reference. This application is also a Continuation in Part of and claims priority to U.S. application Ser. No. 15/089,672, filed Apr. 4, 2016 (hereinafter referred to as "the US utility application"), which is a continuation application of and claims priority to PCT Application No. PCT/IB2014/065112, filed Oct. 7, 2014, which claims priority to Great Britain Application No. 1317752.2, filed Oct. 8, 2013, the entire disclosures of which applications are herein incorporated by reference.

FIELD OF THE INVENTION

The present invention relates to laser treatment devices, specifically laser treatment devices which accommodate more than one handset, a primary and a secondary handset, and cooling mechanisms to cool one or both handsets.

BACKGROUND OF THE PRESENT INVENTION

Figure 1A:
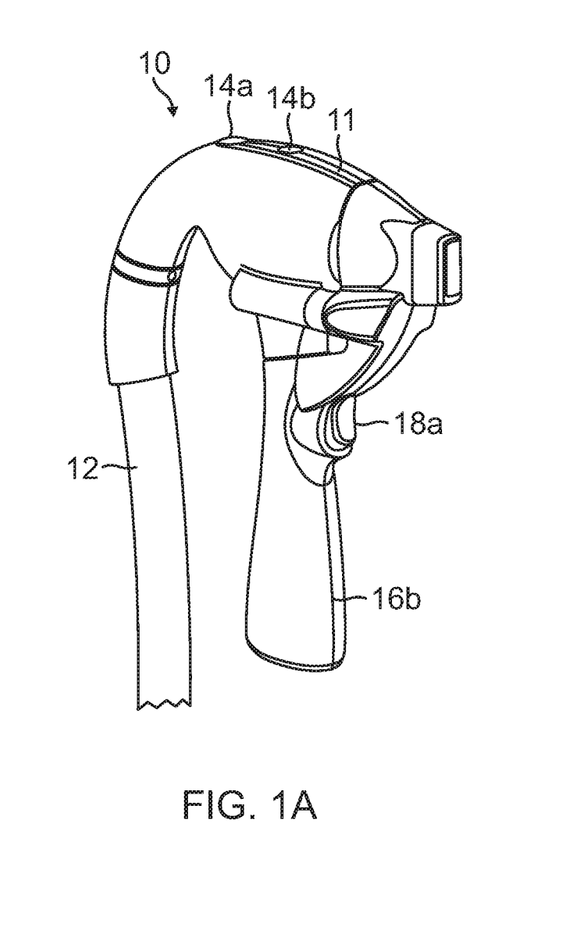
FIG. 1a shows a primary handset and connected auxiliary attachment.
Figure 1B:
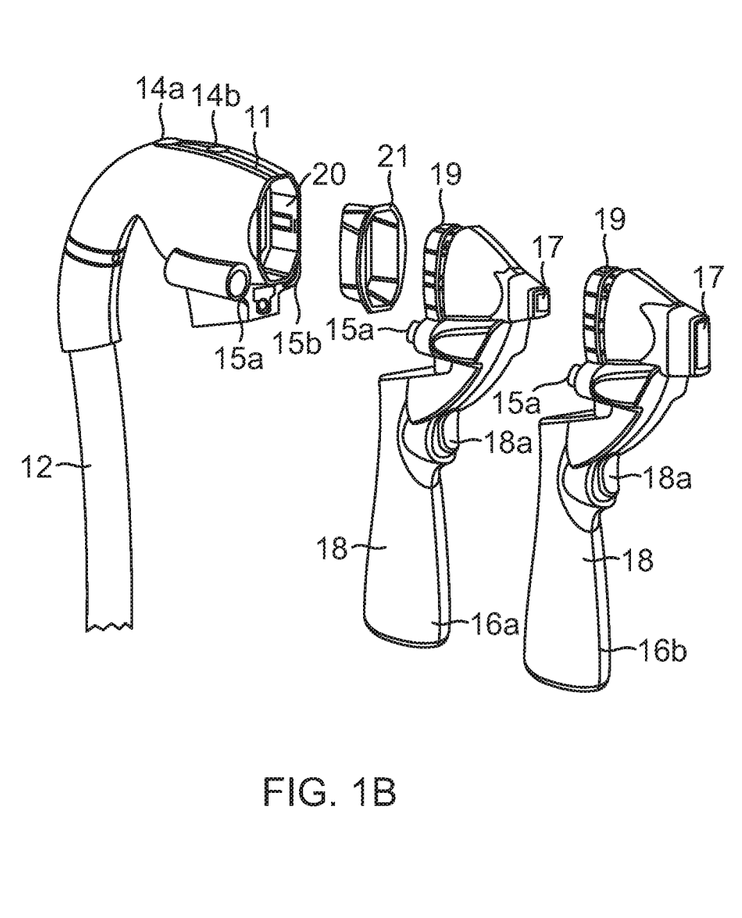
FIG. 1b shows a primary handset with detached alternative attachments.

The US utility application mentioned above includes a primary handset 10 shown in FIG. 1A and an auxiliary handset 18 shown detached from the primary handset in FIG. 1B. The primary and auxiliary handsets are shown joined to one another in FIG. 1A.

Within the primary handset is situated an array of laser diodes which produce laser light as well as heat when fired. The primary handset is also tethered to a console or cabinet which, among other things, includes a cooling system to cool the laser diodes. The auxiliary handset can be attached to the primary handset and harnesses the laser diodes to concentrate and direct laser light to tip windows such as those shown as 17 in FIG. 1B. The tip or tips 17, when impinged upon by laser light from the laser diodes, will also heat up. Since the tips 17 are meant to be placed on the human skin tissue, cooling the tip is desirable to lessen the buildup of heat on the tip and the skin tissue.

Figure 2A:
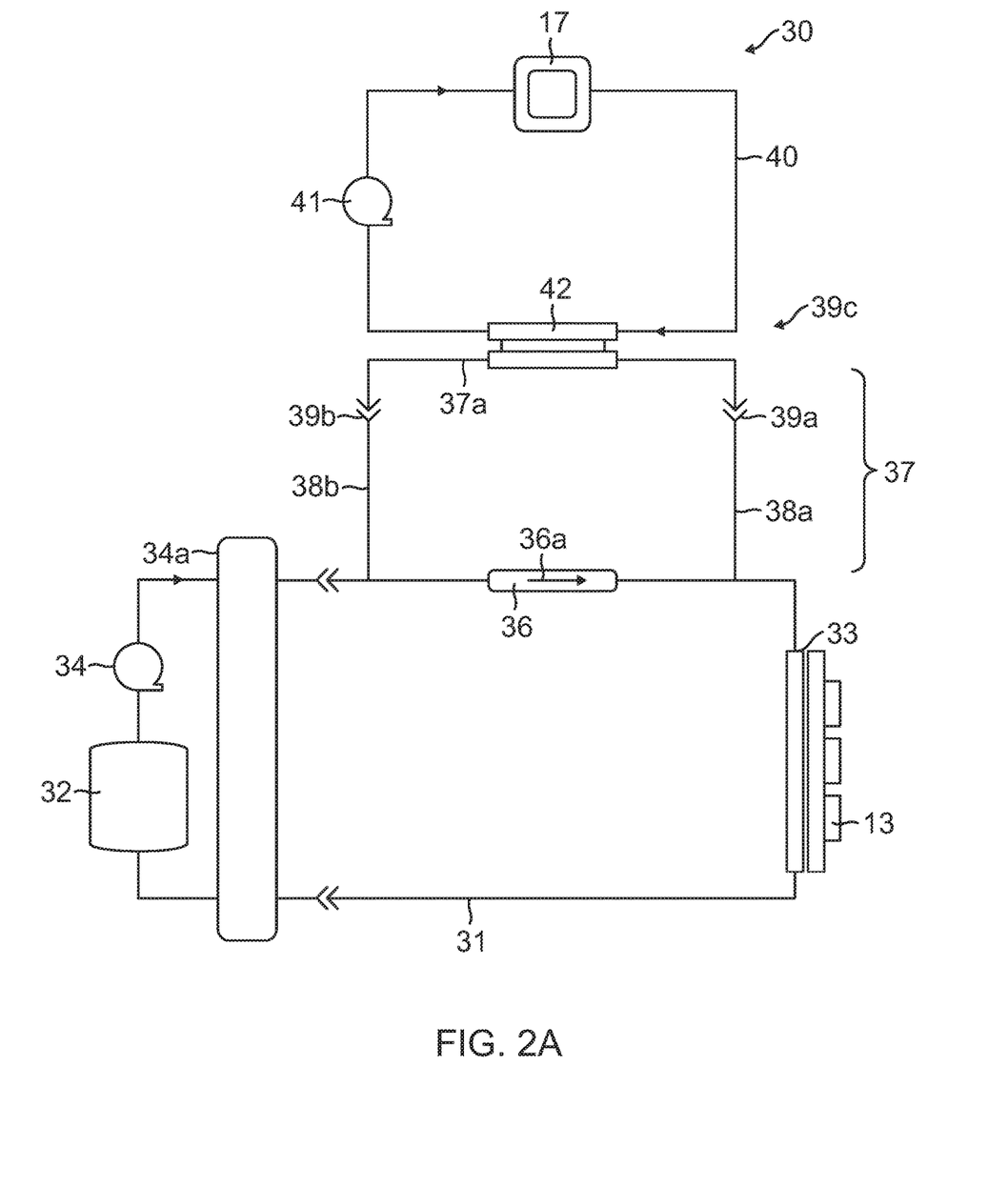
FIG. 2a is an illustration of the cooling circuit of the primary handset and auxiliary attachment.
Figure 2B:
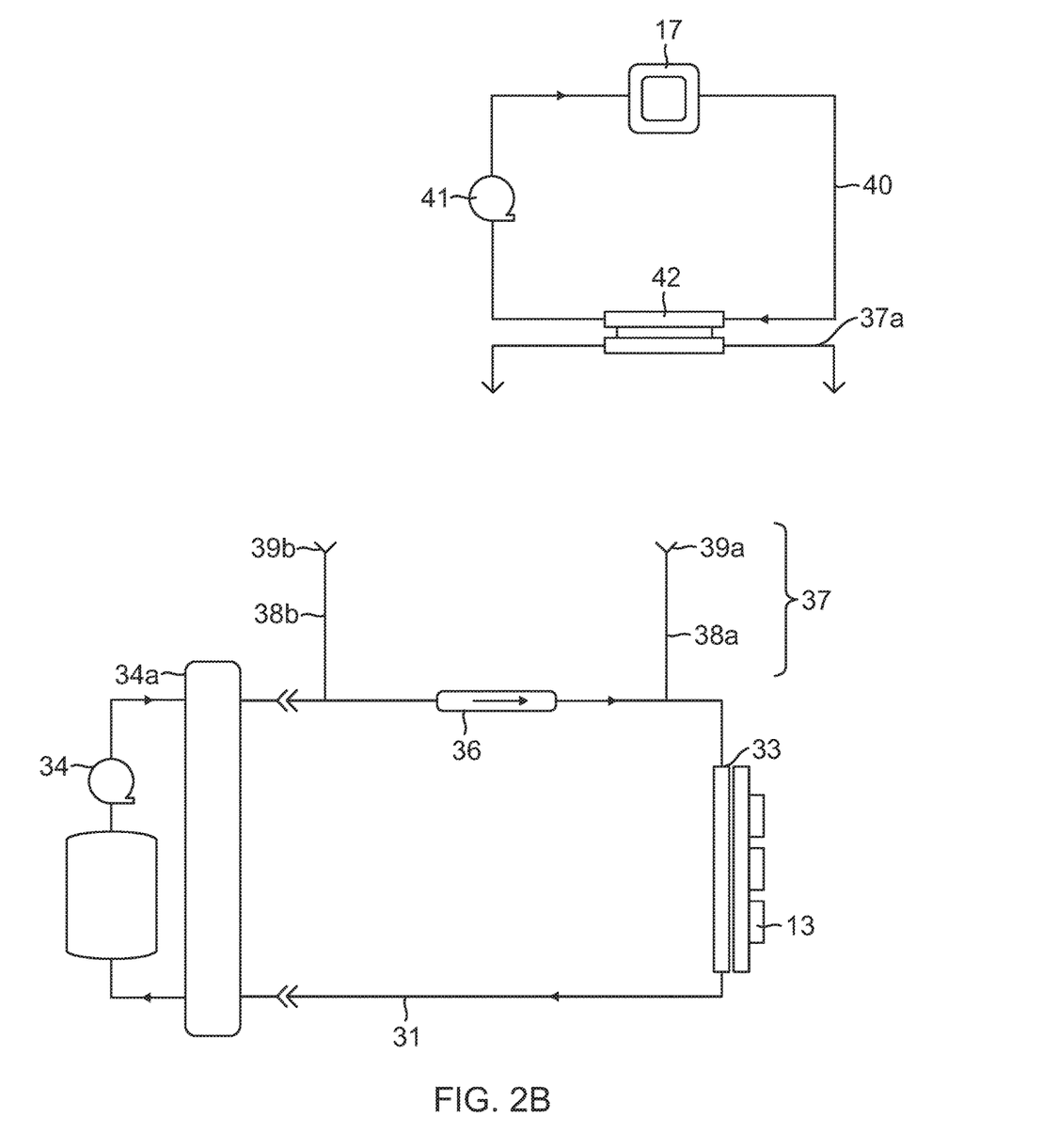
FIG. 2b is an illustration of the operation of cooling circuit of FIG. 2a where no auxiliary attachment is attached to the primary handset.

The cooling system provided is described in the US utility application and is generally of the type that uses a circulating cooling fluid with appropriate heat exchanger(s) to remove heat from the system. In general, the cooling system, shown in FIGS. 2A, 2B and 2C, includes a primary loop and an auxiliary cooling loop, the first such loop lying in the primary handset and the auxiliary loop lying in the auxiliary handset. FIG. 2B shows the auxiliary handset and the primary handset detached from one another. In this setup, the cooling fluid will be restricted to flowing through pump 34 only within the primary loop. However, when the auxiliary handset is joined with the primary handset, the cooling capacity of the primary loop is used to cool the cooling circuit in the auxiliary loop. The point of joinder of both loops is through heat exchanger 42 which dissipates the heat buildup in the tip 17 of the auxiliary handset.

Turning back to FIG. 1B, the points at which the cooling systems are joined are shown as 15a and 15b. Those points are closable/openable conduits through which cooling fluid will flow (or not flow) into the auxiliary handset cooling system, again as described in detail in the US utility application.

The cooling system described in the US utility application provides a clever mechanism by which cooling fluids are diverted into the auxiliary handset. However, a simpler system with fewer parts is desirable and this is the focus of the present invention.

SUMMARY OF THE PRESENT INVENTION

In an aspect, a laser treatment apparatus includes a primary handset and an auxiliary handset, the primary handset being connectable to the auxiliary handset, the primary handset having a laser source having a primary heat exchanger, and a main cooling circuit to provide cooling fluid to the primary heat exchanger to cool the laser source, the cooling circuit having a circuit connection for engagement with the auxiliary handset; the circuit connection comprises one or more fluid connectors for connection to an auxiliary cooling circuit within the auxiliary handset; the cooling circuit within the auxiliary handset includes a secondary heat exchanger; and wherein an electro-mechanical mechanism within the primary handset switches from a first position so that cooling fluid flows in the main cooling circuit within the primary handset when no auxiliary handset is attached and in a second position diverts flow of the cooling fluid to the heat exchanger in the auxiliary handset when the auxiliary handset is connected to the primary handset.

In another aspect, in the laser treatment apparatus, the auxiliary handset includes a tip window to receive and transmit light from the laser source through the tip window.

In yet another aspect, in the laser treatment apparatus, the auxiliary cooling circuit of the auxiliary handset cools the tip window.

In a further aspect, the laser treatment apparatus further includes a controller which controls the electro-mechanical mechanism to switch from the first to the second position or from the second position to the first position.

In yet another aspect, in the laser treatment apparatus, the electro-mechanical mechanism comprises at least one valve, the valve being operable to permit cooling fluid to flow in the main cooling circuit and to block cooling fluid flow to the auxiliary cooling circuit when no auxiliary handset is connected, and to divert cooling fluid flow to the auxiliary cooling circuit when the auxiliary handset is connected.

In yet a further aspect, in the laser treatment apparatus, the auxiliary handset includes one or more points to connect to the one or more fluid connectors on the primary handset; the one or more fluid connectors are normally closed valves that are openable when the one or more points on the auxiliary handset are inserted into the one or more fluid connectors.

In another aspect, the laser treatment apparatus includes one or more pumps to pump cooling fluid around the one or more of the main and the auxiliary cooling circuit.

BRIEF DESCRIPTION OF THE DRAWINGS

An embodiment of the invention is described by way of example only with reference to the accompanying drawings, wherein;

FIG. 2d is an illustration of an alternative embodiment of the cooling circuit of FIG. 2a.

FIG. 2e is an illustration of a switching valve of the cooling circuit of FIG. 2a.

DETAILED DESCRIPTION OF THE PRESENT INVENTION

With specific reference now to the drawings in detail, it is stressed that the particulars shown are by way of example and for purposes of illustrative discussion of the preferred embodiments of the present invention only, and are presented to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Referring now to FIGS. 1a and 1b, a laser treatment apparatus is generally shown at 10. The apparatus 10 comprises a primary handset 11. The primary handset 11 is connected to a base unit (not shown) by an umbilical connection 12, for example to provide a power connection, and connection to a control panel where the operator may set the treatment parameters. The primary handset 11 has a laser source comprising one or more laser diodes 13, as shown in FIG. 2a, and a pair of operator controls shown at 14a, 14b.

The primary handset 11 may be used separately, or with an auxiliary attachment. Auxiliary attachments with small and large tip sizes are shown at 16a and 16b respectively. The auxiliary attachments 16a, 16b are releasably connectable to the primary handset 11 by a latch mechanism, in this example comprising projections 15a on the auxiliary attachment 16a, 16b received in connectors 15b provided on the primary handset 11. The engagement of the projections 15a and connections 15b holds the primary handset 11 and auxiliary attachment 16a, 16b firmly in the correct orientation. An auxiliary attachment 16b is shown connected to the primary handset 11 in FIG. 1a.

Each auxiliary attachment may be configured to have a different treatment area or cone size, so that laser light can be concentrated in a specific treatment area. The auxiliary attachments have a tip window 17, which is cooled as described below to reduce patient discomfort. In addition, each auxiliary attachment has a handle 18, to allow an operator to position and control the apparatus 10, with an auxiliary control 18a provided on the handle 18, in this example in the form of a trigger.

A connecting sleeve 19 extends from an upper part of the auxiliary attachment 16a, 16b and is received in mouth 20 of the primary handset 11. The connecting sleeve 19 and mouth 20 interfit to provide a secure connection, such that laser light cannot escape from the connection between the primary handset 11 and auxiliary attachment 15, 16.

Where the primary handset 11 is used without an auxiliary attachment, a disposable insert 21 may be inserted into the mouth 20 for use with a vacuum system (not shown). The insert 21 will be located against the patient's skin and a vacuum formed within in the insert to draw tissue into the insert. For hygiene, insert 21 is discarded after use.

To provide for cooling of the laser diodes 13 and an auxiliary attachment 16a, 16b (when connected), a cooling apparatus is provided as generally shown at 30 in FIG. 2a. A cooling circuit 31 is provided in the primary handset 11, to provide cooling fluid from a reservoir 32 to a primary heat exchanger 33 to cool the laser diodes 13. A pump 34 is provided to pump cooling fluid from the reservoir 32 around the cooling circuit 31. The pump 34 is operable to pump cooling fluid in one direction, in this example clockwise away from the reservoir. To direct the flow of cooling fluid around the cooling circuit 31 in either of a first, clockwise direction or a second, anticlockwise direction, a switch valve 34a is connected between the pump 34 and reservoir 32, and the cooling circuit 31. The cooling circuit 31 has a main cooling circuit or loop, extending from the reservoir 32, through pump 34, through main loop valve 36, to primary heat exchanger 33 and back to reservoir 32. In the present example main loop valve 36 comprises a uni-directional valve as shown by arrow 36a.

The auxiliary attachments of FIGS. 1A and 1B are each provided with an attachment cooling circuit 40 shown in FIG. 2A. Attachment cooling circuit 40 comprises a closed loop filled with cooling fluid pumped around the loop by pump 41. The attachment cooling circuit passes cooling fluid from attachment heat exchanger 42 to window 17, to cool the window.

To provide for heat exchange with the attachment heat exchanger 42, an auxiliary circuit connection is provided, generally shown at 37. In the embodiment of FIGS. 2a and 2b, the auxiliary attachment has a cooling duct 37a in communication with attachment heat exchanger 42. The auxiliary circuit connection 37 further comprises first branch 38a and second branch 38b connected to main loop 35 either side of the main loop valve 36. Quick release fluid connectors 39a, 39b are provided to connect the cooling duct 37a to first and second branches 38a, 38b in fluid communication, thus defining an auxiliary loop 39c.

When no auxiliary attachment is connected to the primary handset 11, the cooling circuit functions as shown in FIG.

2b. As no auxiliary attachment is connected to fluid connectors 39a, 39b, first and second branches 38a, 38b are closed. Switch valve 34a is operated to pump fluid clockwise as shown by the arrows around the main loop 35, such that fluid passes through main loop valve 36 to primary heat exchanger 33. Accordingly, cooling is provided to laser diodes 13.

Figure 2C:
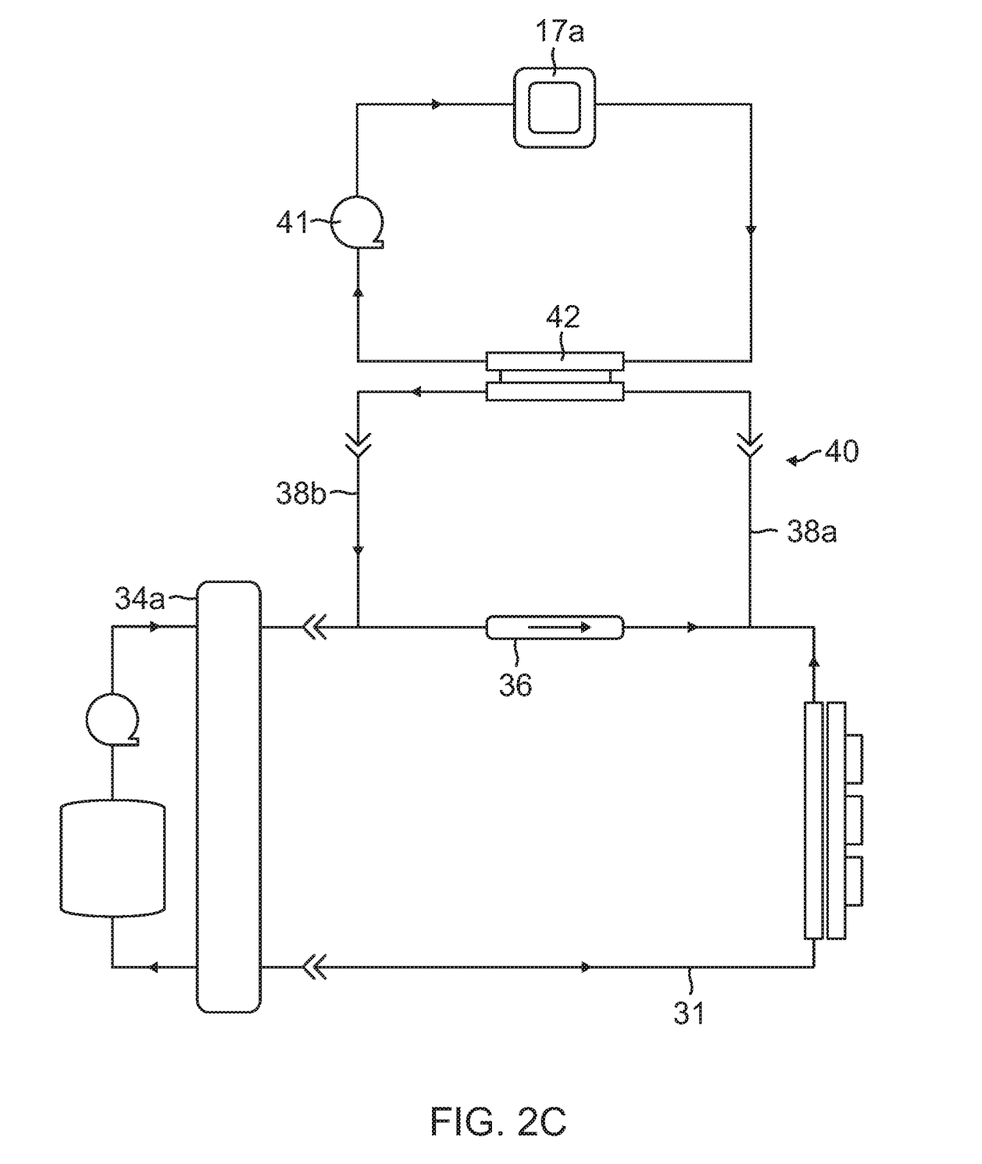
FIG. 2c is an illustration of the operation of the cooling circuit of FIG. 2a where an auxiliary attachment is attached to the primary handset.

When an auxiliary attachment is connected to the primary handset 11, the cooling circuit functions as shown in FIG. 2c. When an auxiliary attachment 15a, 15b is connected, first and second branches 38a, 38b and cooling duct 37a are in flow communication to define auxiliary loop 39c.

Switch valve 34a is operated to direct cooling fluid in an anticlockwise direction as shown in FIG. 2c. After passing through primary heat exchanger 33, the cooling fluid cannot pass through main loop valve 36, and accordingly all fluid is directed through auxiliary loop 39c through attachment heat exchanger 42. Pump 41 operates to pass cooling fluid to cool window 17 and then to heat exchanger 42. The flow rate and cooling liquid volumes in the circuits 31 and 40 are such that fluid passing through the cooling duct side of attachment heat exchanger 42 will be cooler than fluid passing through the attachment side of heat exchanger 42, thus cooling the fluid in the cooling circuit 40.

The arrangement of cooling circuits shown above thus allows multiple alternative attachments to be removably and interchangeably used with a single primary handset, while still provided cooling to the window or instrument tip to be placed against the patient's skin.

Figure 2D:
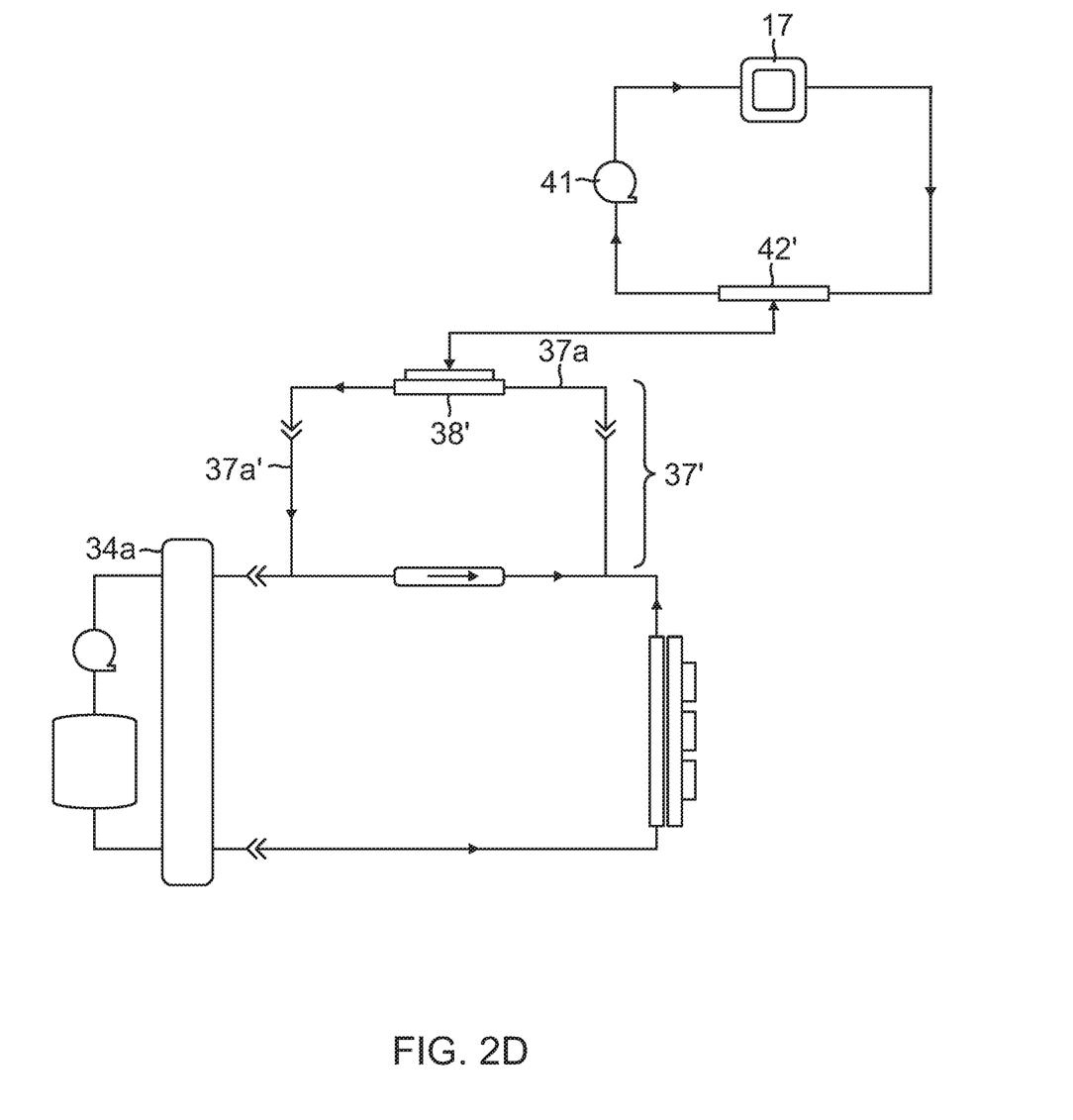

An alternative embodiment is shown in FIG. 2d. In this alternative, attachment cooling circuit 40 passes cooling fluid through attachment heat exchanger 42'. Auxiliary circuit connection 37' comprises a loop 37a' passing through secondary heat exchanger 38', such that secondary heat exchanger 38' is connected in parallel to main loop valve 36.

When no auxiliary attachment is connected to the primary handset 11, the cooling circuit functions as shown in FIG. 2b.

When an auxiliary attachment is connected to the primary handset 11, the cooling circuit functions as in a similar manner to the circuit of FIG. 2c. When an auxiliary attachment 16a, 16b is connected, heat exchangers 38', 42' are held in mutual contact, such that thermal transfer can occur between them. Pump 34 is operated to pump cooling fluid in an anticlockwise direction as shown in FIG. 2d. After passing through primary heat exchanger 33, the cooling fluid cannot pass through main loop valve 36, and accordingly all fluid is directed through secondary heat exchanger 38'. Pump 41 is operating to pass cooling fluid to cool window 17 and then to attachment heat exchanger 42'. The flow rate and cooling liquid volumes in the circuits 31, 40 are such that fluid passing through heat exchanger 38' will be cooler than fluid passing through heat exchanger 42', thus cooling the fluid in the attachment cooling circuit 40.

Figure 2E:
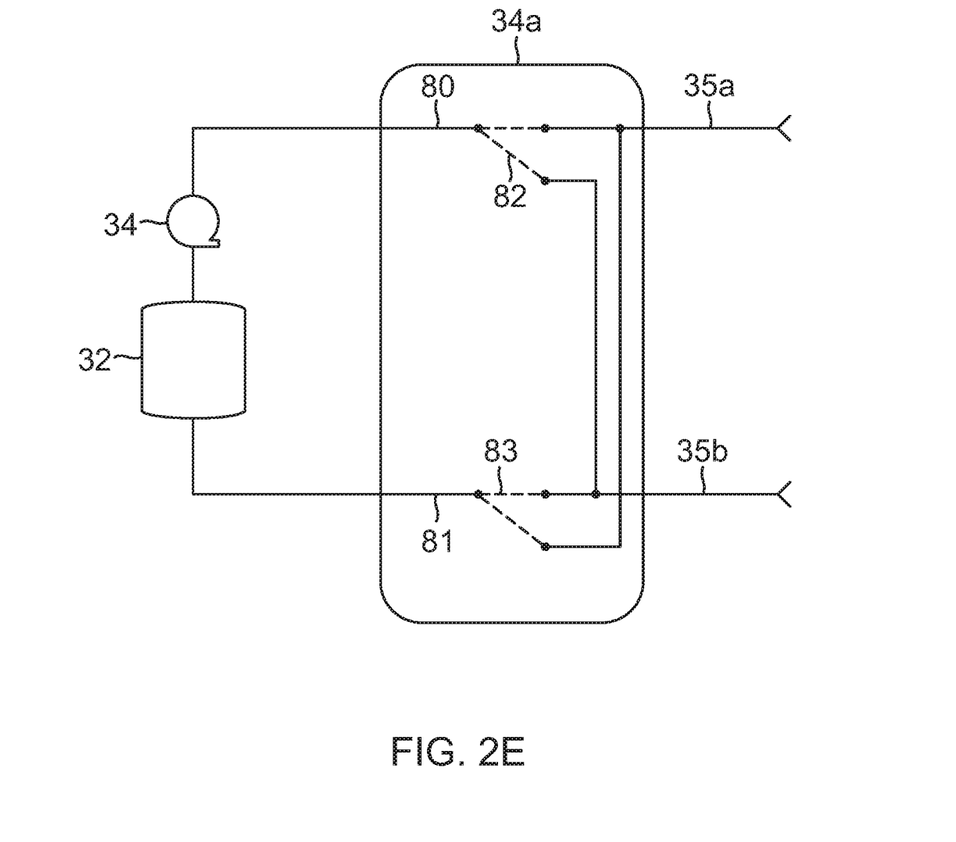

An example of a switch valve 34a is shown in FIG. 2e. Pump 34 is connected to input line 80, and the reservoir 32 to return line 81. A first connection to main loop 35 is shown at 35a and a second connection to main loop 35 is shown at 35b. Coupled selector valves are shown at 82, 83. In a first position, selector valve 82 couples input line 80 to first connection 35a, and selector valve 83 couples second connection 35b to return line 81. In a second position, selector valve 82 couples input line 80 to second connection 35b, and selector valve 83 couples first connection 35a to return line 81. Accordingly, pump 34 is operable to pump cooling fluid in a single direction, clockwise in this diagram, and the switch valve 34a allows the cooling fluid to circulate in either direction around the main loop.

In a further alternative, if reservoir 32 is omitted, pump 34 may be operable to pump cooling fluid in both directions around cooling circuit 31, plus removing the need for switch valve 34a.

Figure 3A:
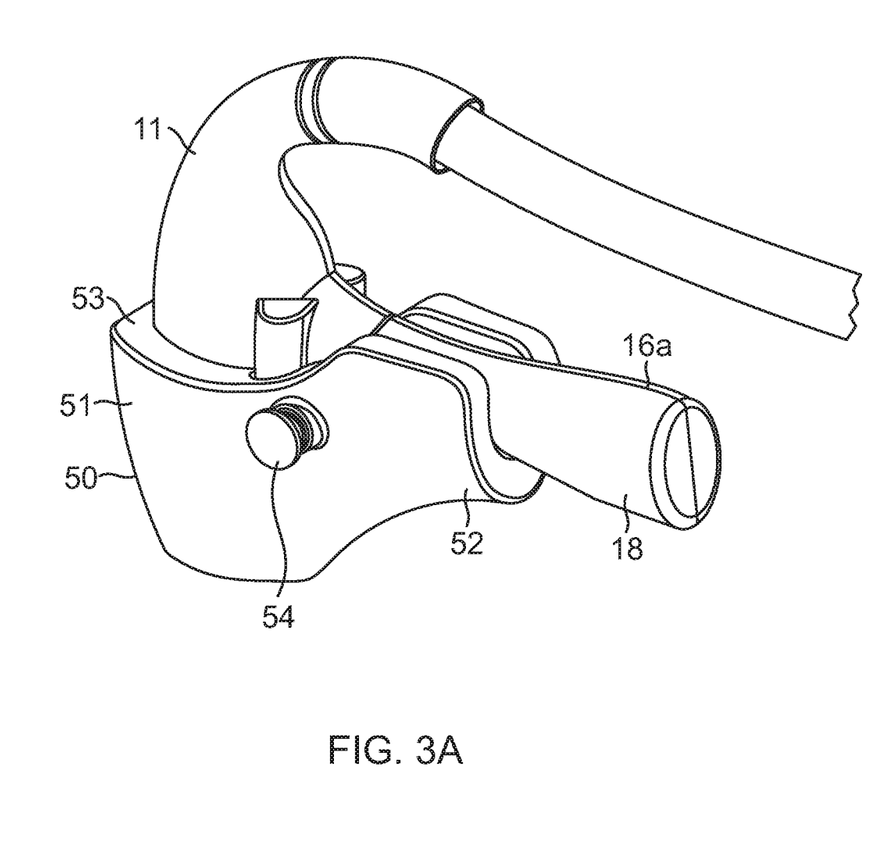
FIG. 3a is a perspective view of a primary handset and auxiliary attachment in a holder.
Figure 3B:
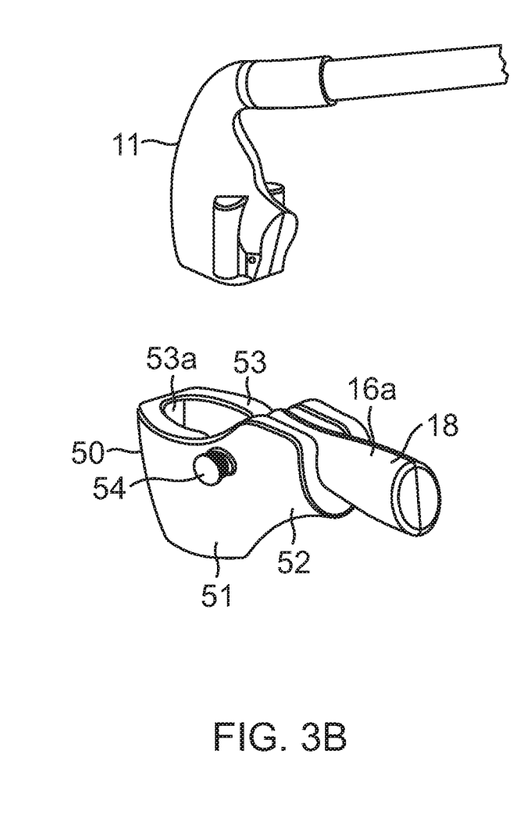
FIG. 3b is a similar view to FIG. 3b wherein the primary handset has been released from the auxiliary attachment.

To hold the auxiliary attachments, the laser treatment system has a corresponding holder for each auxiliary attachment as shown in FIGS. 3a and 3b. The holder is shown at 50, comprising a bowl section 51 to receive the body of the auxiliary attachment and a side cradle 52 to receive the handle 18. As is apparent from the figures, an internal buffer 53 lines the inside of the holder and is shaped to snugly receive the auxiliary attachment 16a, 16b. In this example, internal buffer 53 has an internal cavity 53a which is configured to accept an auxiliary attachment and an external surface 53b configured to fit the interior of holder 50. Different internal buffers 53 can be configured to snugly receive different auxiliary attachments by having suitable internal cavity designs and a common external surface design so a universal holder 50 can be used to hold all auxiliary attachments.

A release button is shown at 54, which may be pressed to release the latch mechanism, enabling the primary handset 11 to be disconnected from the auxiliary attachment 16a, 16b as shown in FIG. 3b. The latch mechanism may be any suitable mechanism, but is preferably configured such that manual or accidental release (i.e., without using release button 54) is difficult, for example by making the latch mechanism difficult to access or resistant to release by other methods. This is advantageous in that the auxiliary attachments 15a, 15b cannot be accidentally released from the primary handset, or cannot be deliberately released and then left in an unsafe position, dropped or damaged. The holder 50 and release button 54 ensure that the primary handset and auxiliary attachment 16a, 16b can only be released when the auxiliary attachment is in its corresponding holder. Preferably, the laser treatment system will have a plurality of holders, each corresponding to one of a plurality of auxiliary attachments.

Figure 4A:
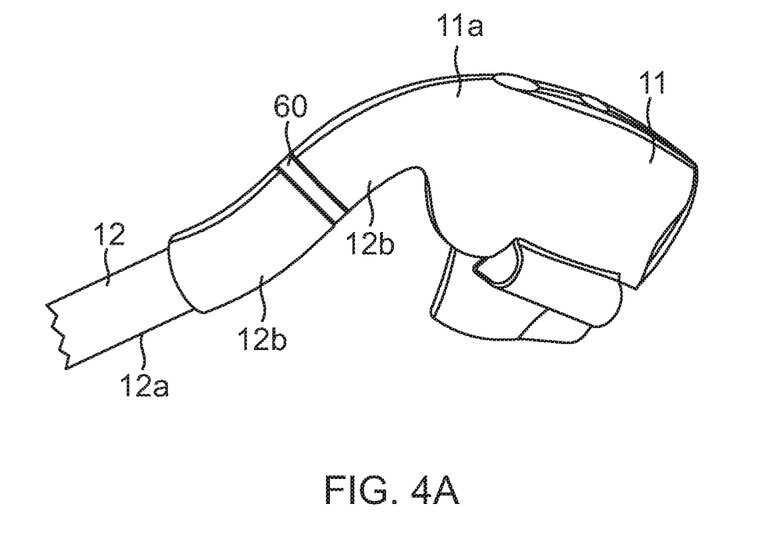
FIG. 4a is perspective view of a primary handset and umbilical connection showing a rotary joint.
Figure 4B:
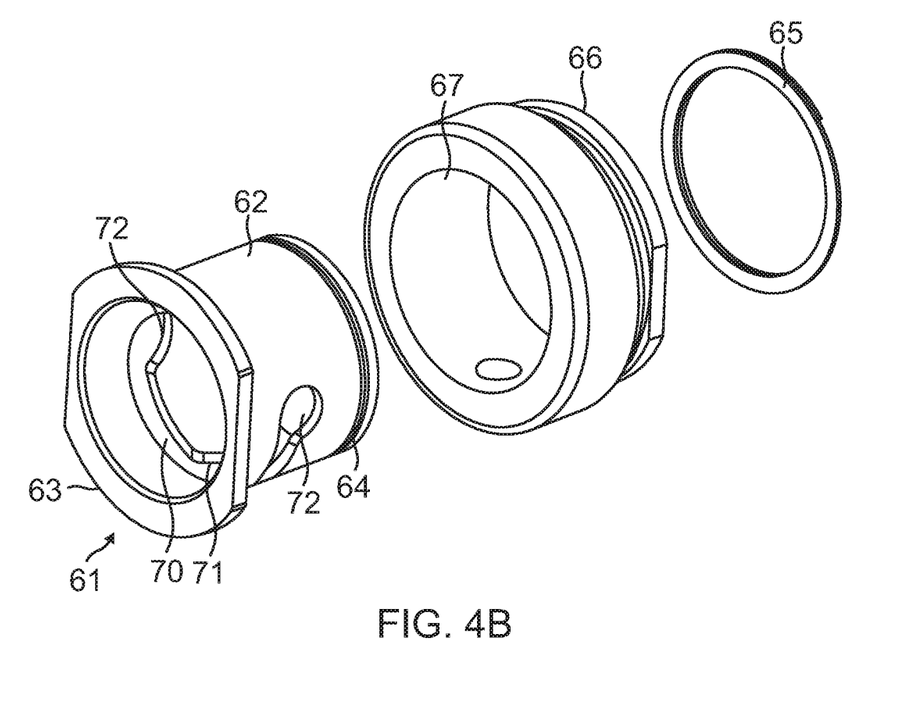
FIG. 4b is an exploded view of the rotary joint.

As shown above, the primary handset 11 is connected to an umbilical connection 12 for connection to a base station. When an auxiliary attachment is connected to the primary handset 11, it may be difficult to comfortably position the apparatus while holding the handle due to the position of the umbilical connection 12 immediately behind the handle 18. To overcome any difficulty, in the present example the primary handset is connected to the umbilical connection via a rotary joint 60, shown in FIGS. 4a to 4d. As shown in FIG. 4a, the umbilical connection 12 has a flexible hose section 12a and a curved, rigid or semi-rigid end part 12b. The primary handset 11 has a rearwardly extending projection 11a of about the same diameter as end part 12b. The rotary joint 60 comprises a first part 61, which has a generally cylindrical section 62 having a flange 63 at one end to engage the end part 12b, and a groove 64 disposed towards the other end to receive a ring clip 65. The rotary joint has a second part 66 having a generally annular shape, with an internal bore 67 shaped to receive the cylindrical portion 62 and a handset connector part 68 to connect to the projection 11a.

Figure 4C:
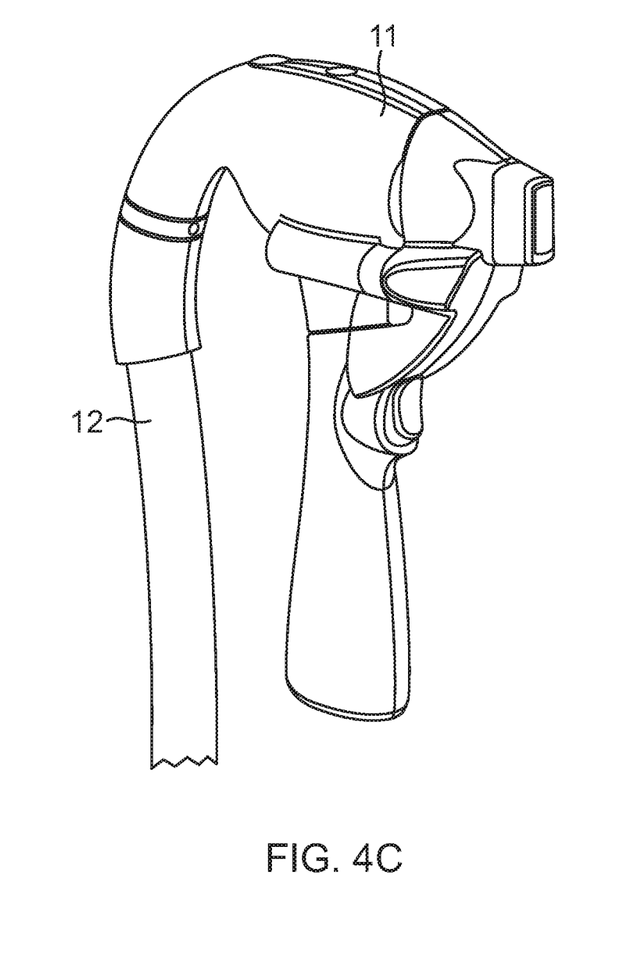
FIG. 4c is a perspective view of a primary handset and auxiliary attachment with the umbilical connection in a first position.
Figure 4D:
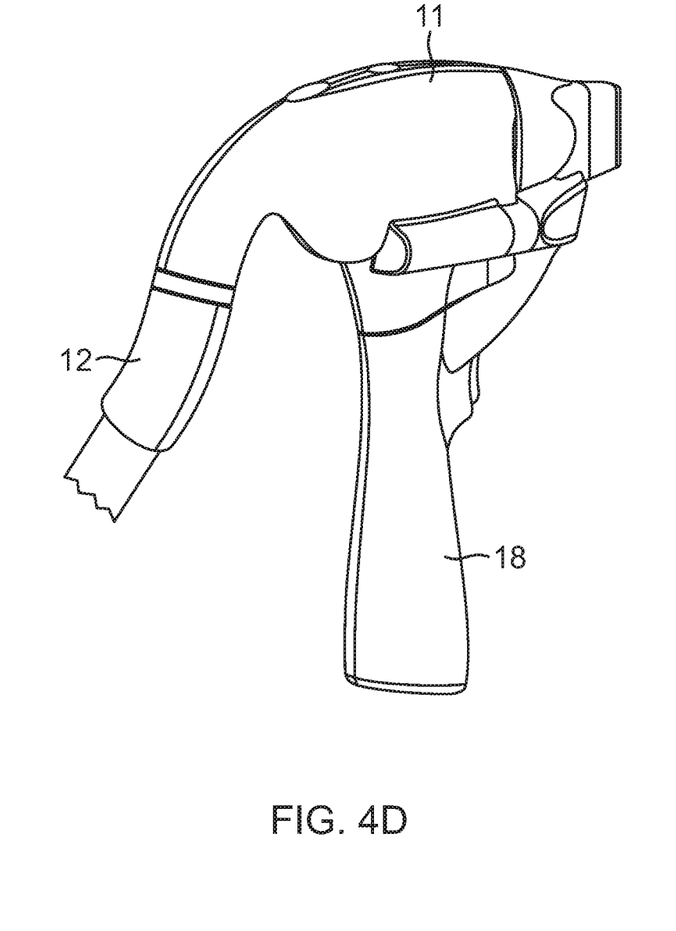
FIG. 4d is a view similar to FIG. 4c showing the umbilical connection in a second position.

The rotary joint 60 enables the first and second parts 61, 66 to be in one of several offset latched positions. A groove 70 extends circumferentially of the cylindrical part 62, connecting larger circular cutouts, a central cutout 71 and offset cutouts 72. In this example the offset cutouts are each offset by 90° around the circumference of the cylindrical part 62 from the central cutout 71. A projection 73 extends inwardly of the bore 67, and is dimensioned to be received in the cutouts 71, 72. When the projection 73 is in one of the cutouts 71, 72, the two parts of the rotary joint 60 are held in a latched position relative to one another. By rotating the handset 11 and end part 12b, the cylindrical portion can be caused to slightly deform, allowing the projection to move to another cutout 71,71, where it will once again be latched in place. FIG. 4c shows the umbilical connection latched in a central position, with projection 73 in central cutout 71. FIG. 4d shows the umbilical connection 12 rotated to the left, such that projection 73 will be in one of the offset cutouts 72, latched in a position away from the handle 18.

Figure 5A:
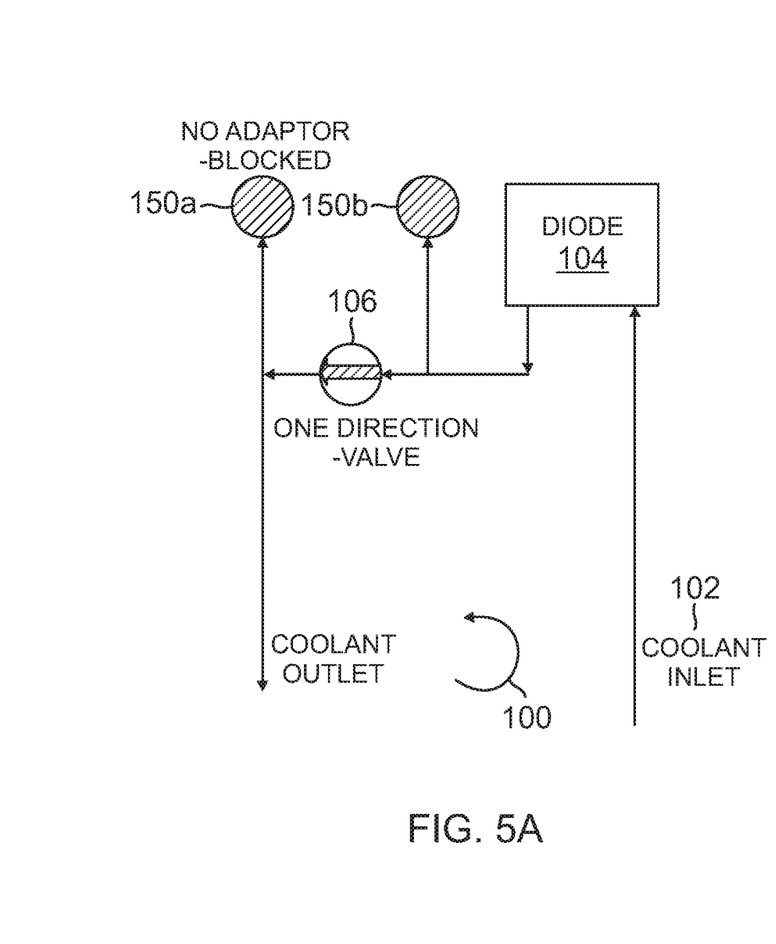
FIGS. 5A and 5B illustrate simplified versions of the structure and operation of the cooling system of FIGS. 2A, 2B and 2C.
Figure 5B:
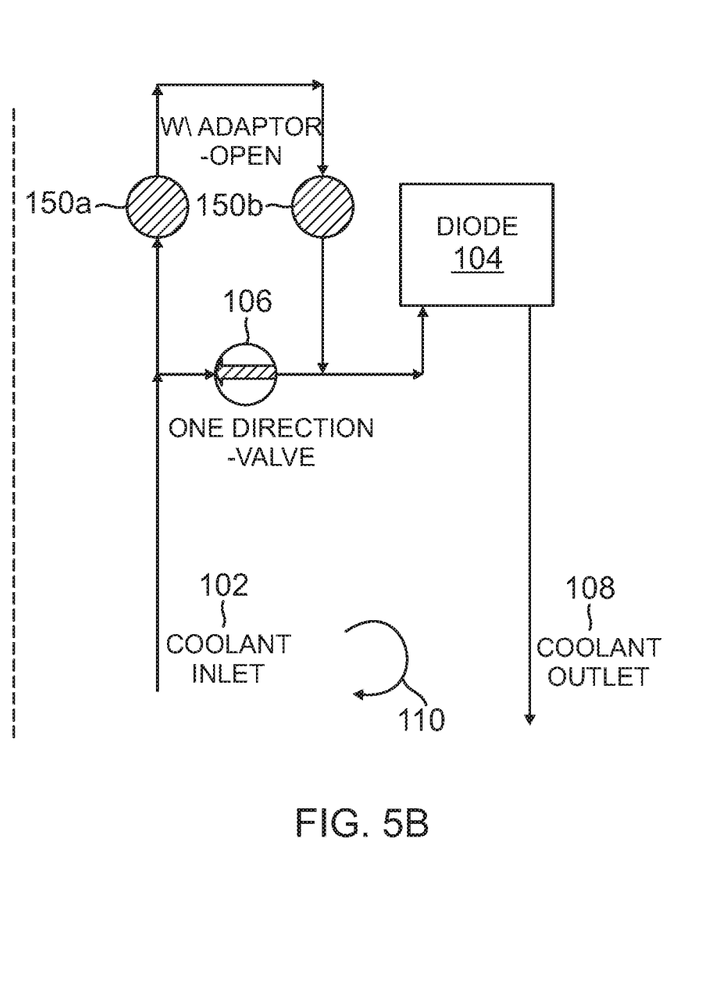

FIG. 5A shows the cooling system operation of FIGS. 2A, 2B and 2C in a simplified version when no auxiliary handset is attached, and FIG. 5B shows the same cooling system operation when an auxiliary handset is attached per the US utility application. As can be seen in FIG. 5A, the coolant flows in a generally counterclockwise direction 100 from inlet 102 to and through diode 104. The fluid moves from the diode 104 through one direction valve 106 and then to the coolant outlet 108. The fluid cannot flow into points 150a or 150b (equivalent to points 15a and 15b in FIG. 2B for example) because those points have self-closing valves since the auxiliary handset is not attached. Now, when an auxiliary handset is attached, as in FIG. 3B, the points and self-closing valves 150a and 150b are open so that cooling fluid can enter the auxiliary handset. In order to drive cooling fluid into the auxiliary handset, the pump (34 in FIG. 2B) is reversed in direction and the flow now becomes generally clockwise, as seen as 110. When the cooling fluid flow is reversed, the flow goes from the cooling inlet 102 towards the auxiliary handset and is constrained to flow into the auxiliary handset since it cannot flow through valve 106, which is a one-way valve and opposes the flow of cooling fluid directly to the diode 104. The cooling fluid then goes through the auxiliary handset cooling system and then out and back into the primary handset towards the diode 104. While operable and well-working in practice, there are a number of parts and electromechanical mechanisms that need to be employed, including the one-way valve 106, a pump that is reversible as well as a switching valve 34a shown in FIG. 2C for example.

Figure 6A:
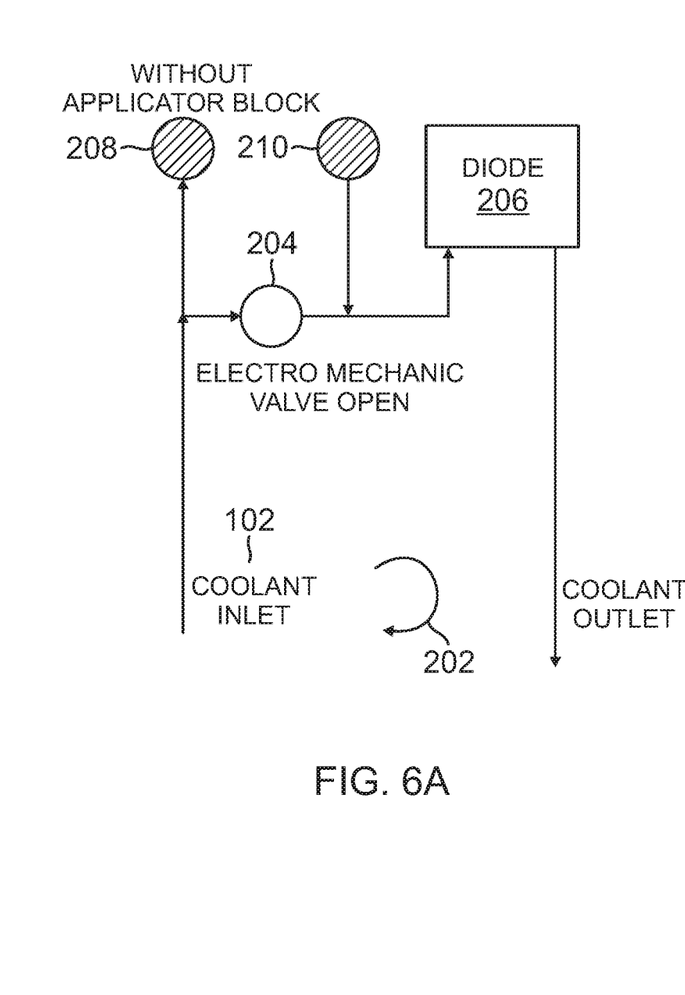
FIGS. 6A and 6B illustrate the structure and operation of the cooling system of the present invention.
Figure 6B:
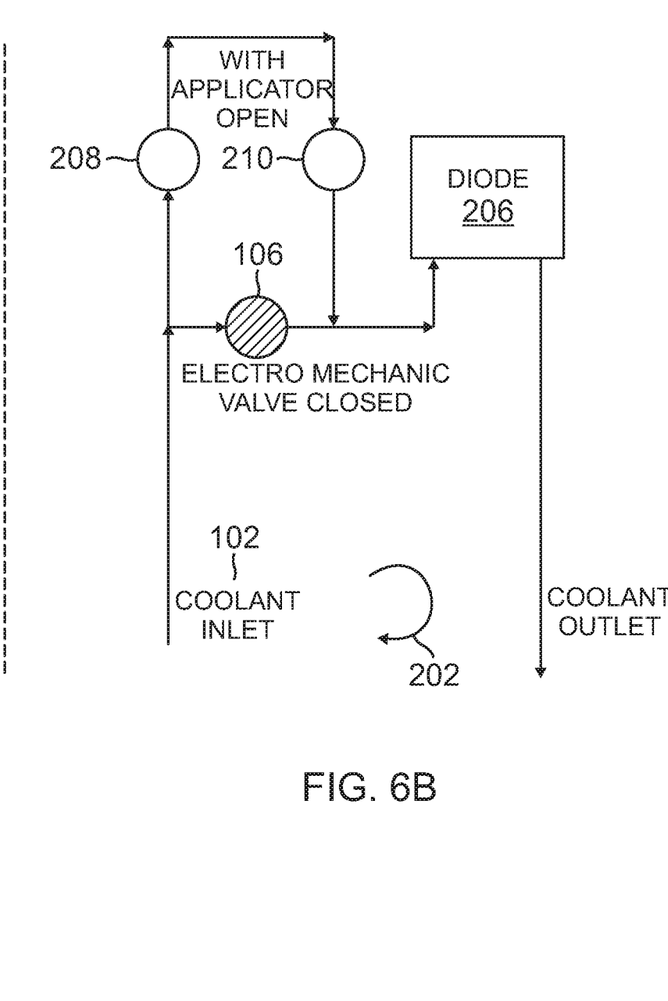

In contrast, the cooling system of the present invention, shown in FIGS. 6A and 6B, eliminates a number of parts and mechanisms, as shown in FIG. 2B, for example. Turning now to FIG. 6A, that figure shows a cooling system in which the flow of cooling fluid is unidirectional in direction 202. While shown as clockwise, it could function just as well in a counterclockwise, but still unidirectional. A simple electromechanical valve 204 replaces all the other mechanisms in the systems of FIG. 2C, for example, including the one-way valve 106 of FIGS. 3A and 3B, a reversible pump 34 (FIG. 2B) and the switching valve 34a (FIG. 2B). In the system illustrated in FIG. 6A, when an auxiliary handset is not attached, the electromechanical valve 204 is open, fluid cannot flow into points 208 and 210 because those points have self-closing valves since the auxiliary handset is not attached and fluid bypasses the not-present auxiliary handset and flows directly to and through the diode 206. A controller associated with the system may be designed to detect the presence or the absence of an auxiliary handset attached to the primary handset. For example, connections 208 and 210 may have one or more suitable known detectors which are connected to the controller such that when an auxiliary handset is attached through connections 208 and/or 210 as in FIG. 6B, the controller may cause the electro-mechanical valve to close so that coolant is constrained to transit through the auxiliary handset as well as through the diode 206. When an auxiliary handset is not connected through connections 206 and/or 210, the electromechanical valve 204 is in an open position constraining the flow of coolant through the diode alone since coolant cannot pass through either connection 208 or 210. When the auxiliary handset is attached, the valve 204 is closed and cooling fluid is constrained to flow first to and through the auxiliary handset cooling system then to and through the diode 206 since flow cannot directly go through the diode. A simple electromechanical switch could be employed to open or close the valve 204 depending on whether the auxiliary handset is attached or not, for example, by use of the above-mentioned suitable known detections.

Thus, a simple valve may be used to replace the plurality of parts and devices in the system described in U.S. utility application Ser. No. 15/089,672.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

Meanings of technical and scientific terms used herein are to be commonly understood as by one of ordinary skill in the art to which the invention belong, unless otherwise defined.

What we claim is:

1. A laser treatment apparatus comprising: a primary handset and an auxiliary handset, the primary handset being connectable to the auxiliary handset, the primary handset having a laser source having a primary heat exchanger, and a main cooling circuit to provide cooling fluid to the primary heat exchanger to cool the laser source, the cooling circuit having a circuit connection for engagement with the auxiliary handset;
   wherein the circuit connection comprises one or more fluid connectors for connection to an auxiliary cooling circuit within the auxiliary handset;
   wherein the cooling circuit within the auxiliary handset includes a secondary heat exchanger; and
   wherein an electro-mechanical mechanism within the primary handset switches from a first position so that cooling fluid flows in the main cooling circuit within the primary handset when no auxiliary handset is attached and a second position which diverts flow of the cooling fluid to the heat exchanger in the auxiliary handset when the auxiliary handset is connected to the primary handset.

2. The laser treatment apparatus of claim 1, wherein the auxiliary handset includes a tip window to receive and transmit light from the laser source through the tip window.

3. The laser treatment apparatus according to claim 2, wherein the auxiliary cooling circuit of the auxiliary handset cools the tip window.

4. The laser treatment apparatus according to claim 1, further comprising a controller which controls the electromechanical mechanism to switch from the first to the second position or from the second position to the first position.

5. The laser treatment apparatus according to claim 1 wherein the electro-mechanical mechanism comprises at least one valve, the valve being operable to permit cooling fluid to flow in the main cooling circuit and to block cooling fluid flow to the auxiliary cooling circuit when no auxiliary handset is connected, and to divert cooling fluid flow to the auxiliary cooling circuit when the auxiliary handset is connected.

6. The laser treatment apparatus of claim 1, wherein the auxiliary handset comprises one or more points to connect to the one or more fluid connectors on the primary handset, wherein the one or more fluid connectors are normally closed valves that are openable when the one or more points on the auxiliary handset are inserted into the one or more fluid connectors.

7. A laser treatment apparatus according to claim 1 comprising one or more pumps to pump cooling fluid around the one or more of the main and the auxiliary cooling circuit.

* * * * *